United States Patent [19]
Baldwin et al.

[11] Patent Number: 5,679,672
[45] Date of Patent: Oct. 21, 1997

[54] BENZODIAZEPINES

[75] Inventors: John J. Baldwin, Rahway, N.J.; David A. Claremon, Maple Glen, Pa.; Jason M. Elliott, London, United Kingdom; Nigel Liverton, Harleysville, Pa.; David C. Remy, North Wales, Pa.; Harold G. Selnick, Ambler, Pa.

[73] Assignee: Merck & Co., Inc., Rahway, N.J.

[21] Appl. No.: 646,249

[22] PCT Filed: Nov. 21, 1994

[86] PCT No.: PCT/US94/13546

§ 371 Date: May 14, 1996

§ 102(e) Date: May 14, 1996

[87] PCT Pub. No.: WO95/14694

PCT Pub. Date: Jun. 1, 1995

Related U.S. Application Data

[63] Continuation of Ser. No. 155,669, Nov. 22, 1993, abandoned.

[51] Int. Cl.[6] .................. A61K 31/55; C07D 487/04
[52] U.S. Cl. .................. 514/220; 540/558; 540/559; 540/560; 540/562; 540/563; 540/564; 540/566
[58] Field of Search .................. 540/558, 559, 540/560, 562, 563, 564, 566; 514/220

[56] References Cited

U.S. PATENT DOCUMENTS 4,663,321  5/1987  Bock et al. .................. 514/220

*Primary Examiner*—Robert T. Bond
*Attorney, Agent, or Firm*—Sylvia A. Ayler; Mark R. Daniel

[57] ABSTRACT

Compounds of structures (I) and (Ia) are Class III antiarrhythmic agents

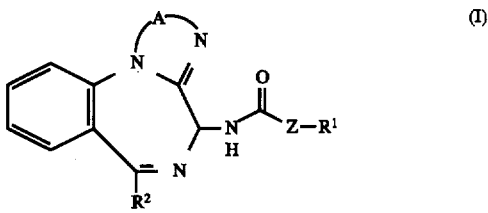

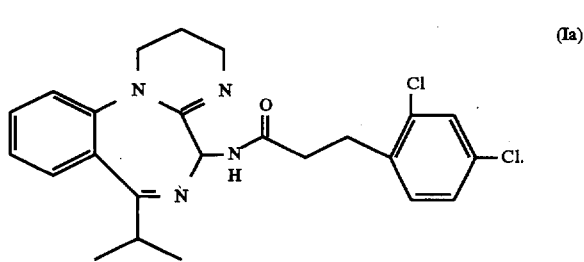

7 Claims, No Drawings

BENZODIAZEPINES

This application is a 371 of PCT/US94/13546 filed 21 Nov. 1994 which claims priority of U.S. application a continuation of Ser. No. 08/155,669, filed 22 Nov. 1993, now abandoned.

SUMMARY OF THE INVENTION

This invention is concerned with novel compounds of general structural formula I:

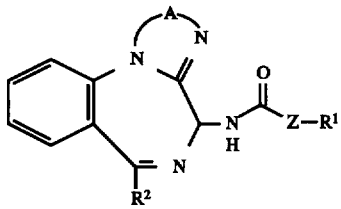

The invention is also concerned with pharmaceutical formulations comprising one or more of the compounds as active ingredient, either alone or in combination with one or more of a Class I, Class II or Class IV antiarrhythmic agent.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrythmic agents are now available on the market, those, having both satisfactory effects and high safety, have not been obtained. For example, antiarrhythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drags which cause a selective prolongation of the duration of the action potential without a significant depression of the Vmax. Drags in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drags of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

DETAILED DESCRIPTION OF THE INVENTION

The novel compound this invention has structural formula I:

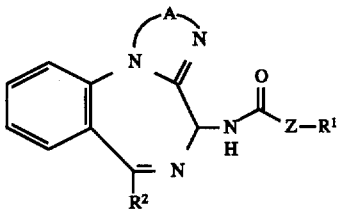

or a pharmaceutically acceptable salt thereof, wherein

A is a 2 or 3 membered chain which is all carbon or one and only one member can be nitrogen or oxygen, which is unsubstituted or substituted on carbon with
1) $C_{1-3}$ alkyl either unsubstituted or substituted with hydroxy,
2) $C_{1-3}$ alkoxycarbonyl or
3) oxo;

Z is
1) $C_{2-3}$ alkenylene or
2) 2- or 3-membered saturated chain, either all carbon or including not more than one heteroatom selected from —NH— —S— or —O—;

$R^1$ is
1) $C_{5-7}$ cycloalkyl,
2) phenyl, either unsubstituted or substituted with up to 2 substituents selected from Cl, Br, I, F, $CF_3$ or $C_{1-3}$ alkyl;

$R^2$ is
1) phenyl,
2) —$NR^3R^4$, wherein $R^3$ and $R^4$ are independently $C_{1-3}$ alkyl or $C_{5-7}$ cycloalkyl,
3) $C_{1-5}$ alkyl or
4) $C_{5-6}$ cycloalkyl.

Representative of the novel compounds of this invention are the following:

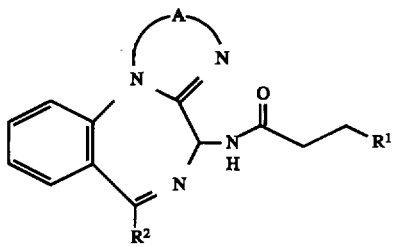

| A | $R^1$ | $R^2$ |
|---|---|---|
| ⌐┐ | cyclohexyl | Ph |
| ⌒ | cyclohexyl | Ph |
| ⌐┐ CH₃ | cyclohexyl | Ph |
| ⌐┐ | 2,4-di Cl Ph | Ph |
| ⌒ | 2,4-di Cl Ph | Ph |

-continued

| A | R¹ | R² |
|---|---|---|
| ⌐CH₃ (cyclopropyl-like) | 2,4-di Cl Ph | Ph |
| ⌐COOCH₃ | 2,4-di Cl Ph | Ph |
| ⌐= (cyclobutene) | 4-CF₃Ph | Ph |
| ⌐= | 2,4-di Cl Ph | Ph |
| ⌐=N | cyclohexyl | Ph |
| ⌐=N | 2,4-di Cl Ph | Ph |
| ⌐CH₃ | 2,4-di Cl Ph | i Pr |
| CH₃⌐ | 2,4-di Cl Ph | i Pr |
| ⌐ | 2,4-di Cl Ph | i Pr |
| H₃C⌐ | 2,4-di Cl Ph | i Pr |
| ⌐CH₃ | cyclohexyl | Ph |
| ⌐O=/O | cyclohexyl | Ph |
| ⌐CH₂OH | 2,4-di Cl Ph | Ph |
| ⌐ | cyclohexyl | —N(CH₃)(cyclohexyl) |

This invention is meant to include the individual diastereomers, where such exist and mixtures thereof and enantiomers and mixtures of the enantiomers.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The novel compounds of the present invention, have the pharmacological properties required for the antiarrhythmic agents of Class III, namely the prolongation of the myocardial action potential in vitro, without a significant depression of the Vmax, and the prolongation of QTc-interval in anesthetized dogs.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

The novel compounds or pharmaceutically acceptable :salts thereof, are administered in an amount ranging from about 0.0001 to about 20 mg per kg or body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The activity of the compounds described herein as antiarrhythmic agents is measured by their ability to block the IKs and/or IKr currents as determined by the following test protocol.

Outward potassium currents are measured in single guinea pig ventricular myocytes using a whole-cell voltage clamp technique described in detail elsewhere (Sanguinetti and Jurkiewicz, 1990. Two components of cardiac delayed actifier $K^+$ current: differential sensitivity to block by Class El antiarrhythmic agents. *J. Gen Physiol.* 96:195–215). Myocytes are isolated by enzymatic (collagenase and protease) digestion of Langandoff perfused hearts. Single cells are them voltage clamped using 1 mm square-bore pipettes filled with 0.5M Kgluconate, 25 mM KCl, 5 mM K(2)ATP. Cells are bathed in a solution containing, in mN: 132 NaCl, 4KCl, 1.2 MgCl[2], 10 HEPES, 10, glucose: pH 7.2, temp. 35° C.

Each cell is maintained at a holding potential of −50 mV. Test depolarizations are applied as voltage ramps from −85 to −50 mV, and as steps to −10 mV (0.5 s) and +50 mV (1.0 s). I[KI] is measured as peak outward current during the voltage ramp. I[Kr] is measured as tail currents upon repolarization from −10 mV to −50 mV. I[KS] is measured as time-dependent current during the pulse to +50 mV. Currents are measured during control, then after exposure to drug at two different concentrations.

Employing this test the compounds described herein have an IC$_{50}$ of less than 1000 nM as IKs and/or IKr blockers.

A novel process for preparing novel compounds of this invention comprises treating a compound of Formula II with a sulfonyl chloride such as methanesulfonyl chloride, benzene sulfonyl chloride or toluenesulfonyl chloride in an organic solvent methylene dichloride, chloroform, tetrachloroethane or the like in the presence of a strong organic base such as diisopropylethylamine.

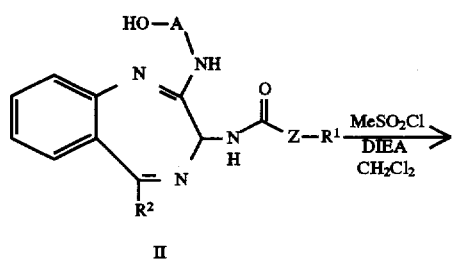

II

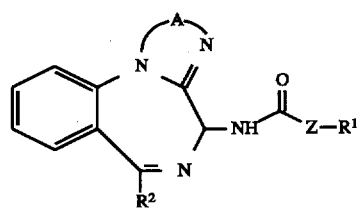

Another novel process for preparing some of the novel compounds of this invention is exemplified by the following:

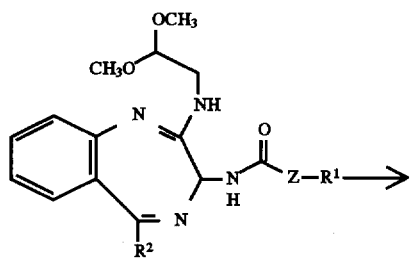

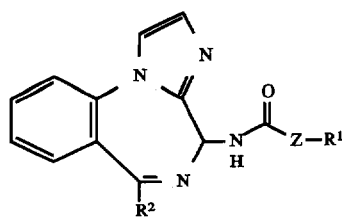

In this process a hemiacetal is dissolved in 50% (v/v) sulfuric acid and treated with mercuric chloride with stirring at room temperature for about 16 to 24 hours.

Alternatively, the hemiacetal starting material is treated with boron trifluoride etherate in a chlorinated alkane such as methylene chloride at about 40°–60° C. until the reaction is complete which occurs in about 1.5 to 3 hours.

A third novel process for preparing some of the novel compounds of this invention is depicted as follows:

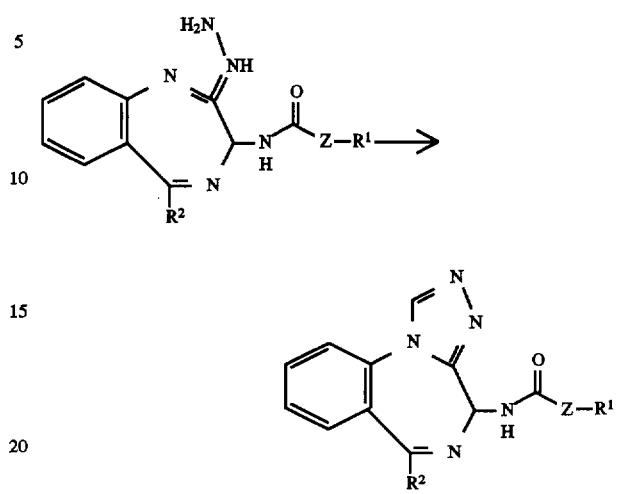

In this process the hydrazone in a lower alkanol, preferably ethanol is treated with triethylorthoformate and refluxed for about 30 minutes to about 2 hours.

A fourth novel process of this invention is depicted as follows:

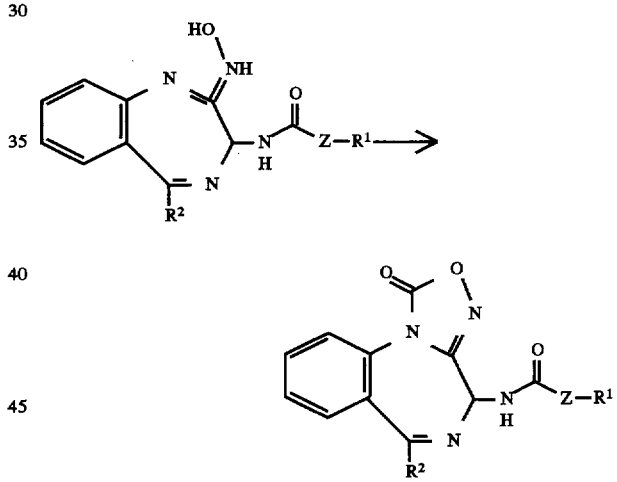

In this process the oxime in an ethereal solvent such as THF, is treated with carbonyldiimidazole and refluxed for about 30 minutes to about 2 hours.

A fifth novel process of this invention is depicted as follows:

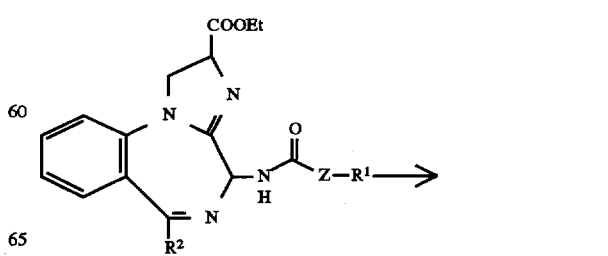

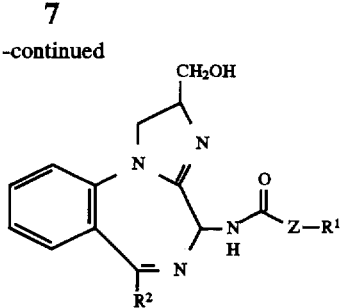

In this process the ester in THF or similar solvent is treated with lithium borohydride at about room temperature for about 16 to about 24 hours.

EXAMPLE 1

3-Cyclohexyl-N-{2,4-dihydro-6-phenyl-1H-imidazo[1,2-a][1,4]benzodiazepin-4-yl}propanamide Step A Phenylmethyl N-[(2,3-dihydro-5-phenyl-2-thioxo-1H-1,4-benzodiazepin-3-yl)]carbamate

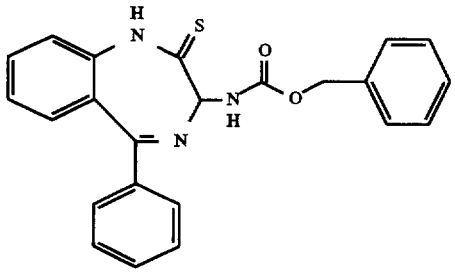

A mixture of (+)-phenylmethyl N-[(3R)-2,3-dihydro-5-phenyl-2-oxo-1H-1,4-benzodiazepin-3-yl]carbamate (4.0 g, 10 mmol) and 2,4-bis(4-methoxyphenyl)-1,3-dithia-2,4-diphosphetane-2,4-disulfide (4.5 g 11 mmol) in toluene (100 mL) was heated under reflux for 75 min. The mixture was cooled and the volume was reduced to 30 mL by evaporation under reduced pressure. The residue was purified by flash column chromatography on silica gel, eluting with EtOAc/Hexane (75:25) to give phenylmethyl N-[(3R)-2,3-dihydro-5-phenyl-2-thioxo-1H-1,4-benzodiazepin-3-yl]carbamate.

$\delta H(d_6\text{-DMSO})$ 10.85 (1H, s), 8.42 (1H, d, J 8.6 Hz), 7.65–7.10 (14H, m), 5.10 (2H, s), and 5.05 (1H, d, J 8.6 Hz).

Step B

3-Cyclohexyl-N-(2,3-dihydro-5-phenyl-2-thioxo-1H-1,4-benzodiazepin-3-yl)propanamide

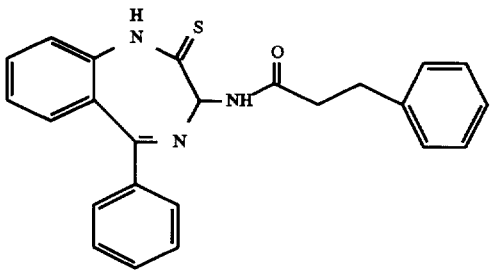

Hydrogen bromide was bubbled at room temperature through a solution of (+)-phenylmethyl N-[(3R)-2,3-dihydro-5-phenyl-2-thioxo-1H-1,4-benzodiazepin-3-yl] carbamate (0.9 g, 2.1 mmol), acetic acid (5 mL) and dichloromethane (5 mL). After 2 h., the solvent was evaporated under reduced pressure, ether was added and the solid was collected and dried in vacuo. A sample (0.58 g, 1.8 mmol) was suspended in THF (10 mL), triethylamine (0.24 mL, 0.18 g, 1.8 mmol) was added and the mixture was stirred at room temperature for 3 h. In a separate flask, oxalyl chloride (0.20 mL, 0.29 g, 2.3 mmol) was added to a solution of cyclohexanepropionic acid (0.33 mL, 0.30 g, 1.9 mmol) and DMF (1 drop) in THF (10 mL) and the mixture was stirred at room temperature for 3 h. The two mixtures were combined, triethylamine (0.32 mL, 0.23 g, 2.3 mmol) was added and the mixture was stirred at room temperature for 2.5 h. The solvent was evaporated under reduced pressure, water was added and the mixture was extracted with ethyl acetate. The combined organic fractions were washed with water, saturated aqueous sodium hydrogen carbonate, water (2×) and brine, dried ($Na_2SO_4$) and the solvent was evaporated under reduced pressure. The residue was purified by flash column chromatography on silica gel, eluting with $CH_2Cl_2$/MeOH (99.5:0.5) and the residue was recrystallized from EtOAc/Hexane to give 3-cyclohexyl-N-(2,3-dihydro-5-phenyl-2-thioxo-1H-1,4-benzodiazepin-3-yl) propanamide as a solid. m.p. 113°–119° C.

$\delta H(CDCl_3)$ 9.8 (1H, br s), 7.75–7.25 (10H, m), 5.75 (1H, d, 18.1 Hz), 2.41 (2H, m), and 1.80–0.85 (13H, m).

Anal. Calcd. for $C_{24}H_{27}N_3OS \cdot 0.8CH_2Cl_2$: C, 62.91; H, 6.09; N, 8.87. Found: C, 62.88; H, 5.70; N, 9.12%.

Employing the procedure substantially as described above in Example 1, Steps A and B but substituting an appropriate acid for the cyclohexanepropionic acid used in Step B the following compounds were prepared:

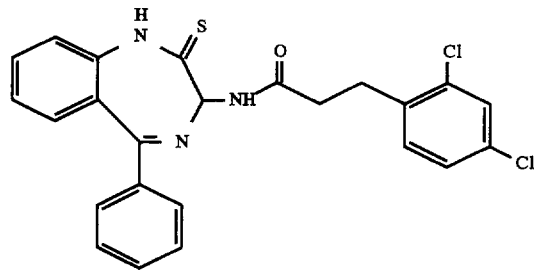

N-(2,3-Dihydro-5-phenyl-2-thioxo-1H-1,4-benzodiazepin-3-yl)-3-(2,4-dichlorophenyl)propanamide $\delta H(CDCl_3)$ 9.65 (1H, br s), 7.70–7.15 (13H, m), 5.75 (1H, d, J 8.4 Hz), 3.15 (2H, t, J 7.2 Hz), and 2.75 (2H, t, J 7.2 Hz).

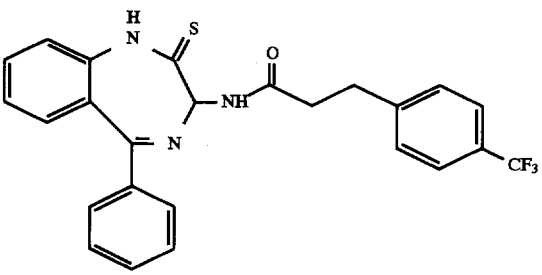

N-(2,3-Dihydro-5-phenyl-2-thioxo-1H-1,4-benzodiazepin-3-yl)-3-(4-trifluoromethylphenyl)propanamide

EXAMPLE 2

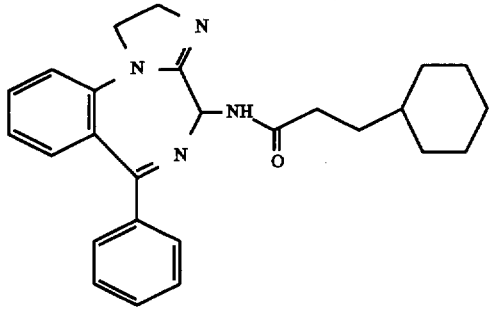

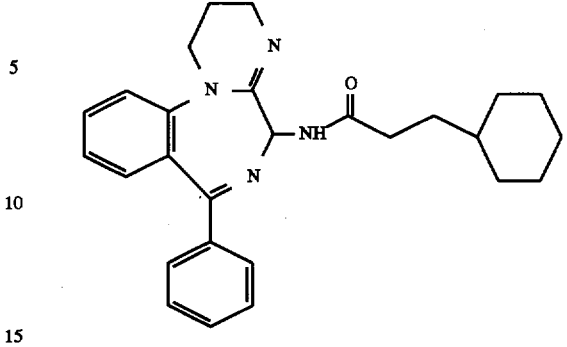

3-Cyclohexyl-N-{2,4-dihydro-6-phenyl-1H-imidazo[1,2-a][1,4]benzodiazepin-4-yl}propanamide A mixture of 3-cyclohexyl-N-(2,3-dihydro-5-phenyl-2-thioxo-1H-1,4-benzodiazepin-3-yl)propanamide (162 mg, 0.4 mmol), 2-aminoethanol (96 μL, 98 mg, 1.6 mmol) and mercuric chloride (141 mg, 0.52 mmol) in THF (5 mL) was stirred at 55° C. for 1 h. The solvent was evaporated under reduced pressure and the residue was triturated with EtOAc/Hexane. The solid was collected and dried in vacuo to give 3-cyclohexyl-N-[2,3-dihydro-2-(2-hydroxyethylimino)-5-phenyl-1H-1,4-benzodiazepin-3-yl)propanamide as a solid (120 mg, 69%). A sample (90 mg, 0.2 mmol) was dissolved in dichloromethane (7 mL), cooled to 0° C. and methanesulfonyl chloride (19 μL, 28 mg, 2.4 mmol) and diisopropylethylamine (75 μl, 56 mg, 0.43 mmol) were added. The mixture was stirred at 0° C. for 30 min., then at room temperature for 2 h. The solvent was evaporated under reduced pressure, toluene was added and the solvent was evaporated under reduced pressure. The residue was purified by flash column chromatography on silica gel, eluting with CH$_2$Cl$_2$/MeOH (98:2) to give 3-cyclohexyl-N-{2,4-dihydro-6-phenyl-1H-imidazo[1,2-a][1,4]benzodiazepin-4-yl}propanamide as a solid (40 mg, 48%), m.p. 202°–208.5° C.

δH(CDCl$_3$) 7.55–7.00 (10H, m), 5.85 (1H, d, J 8.2 Hz), 4.20–3.70 (4H, m), 2.37 (2H, t, J 8.0 Hz), and 1.80–0.80 (13H, m).

Anal. Calcd. for C$_{26}$H$_{30}$N$_4$O.0.4CH$_3$OH.0.1 (C$_2$H$_5$)$_2$O: C, 74.03; H, 7.56; N, 12.89. Found: C, 73.73; H, 7.29; N, 13.00%.

Employing the procedure substantially as described above in Step C but substituting an appropriate N-(2,3-dihydro-5-phenyl-2-thioxo-1H-1,4-benzodiazepin-3-yl)propanamide for the 3-cyclohexyl-N-(2,3-dihydro-5-phenyl-2-thioxo-1H-1,4-benzodiazepin-3-yl)propanamide and an appropriate aminoalcohol for the 2-aminoethanol, the following compounds were prepared:

3-Cyclohexyl-N-{7-phenyl-1,2,3,5-tetrahydropyrimido[1,2-a][1,4]-benzodiazepin-5-yl}propanamide
m.p. 193°–194.5° C.
δH(CDCl$_3$) 7.90 (1H, br s), 7.65–7.10 (9H, m), 5.60 (1H, br s), 4.00–3.40 (4H, m), and 2.45–0.85 (17H, m).
Anal. Calcd. for C$_{27}$H$_{32}$N$_4$O.0.25EtOAc: C, 74.64; H, 7.61; N, 12.43. Found: C, 74.61; H, 7.54; N, 12.37%.

EXAMPLE 3

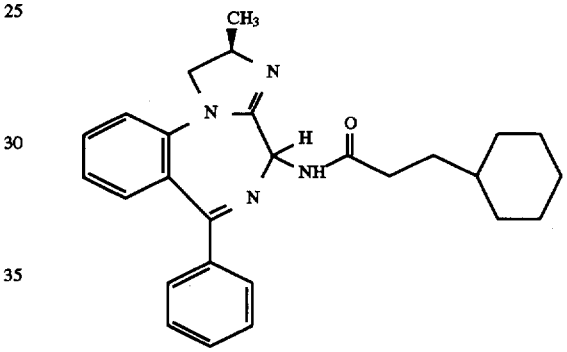

(2R)-3-Cyclohexyl-N-{2,4-dihydro-2-methyl-6-phenyl-1H-imidazo[1,2-a][1,4]benzodiazepin-4-yl}propanamide
δH(CDCl$_3$) (Mixture of diastereoisomers) 7.65–7.00 (10H, m), 5.85 (1H, d, J 8.0 Hz), 4.30–3.80 (3H, m), 2.40 (2H, t, J 8.0 Hz), and 1.80–0.85 (16H, m).
Anal. Calcd. for C$_{27}$H$_{32}$N$_4$O.0.35CH$_2$Cl$_2$: C, 71.68; H, 7.19; N, 12.22. Found: C, 71.83; H, 7.31; N, 12.11%.

EXAMPLE 4

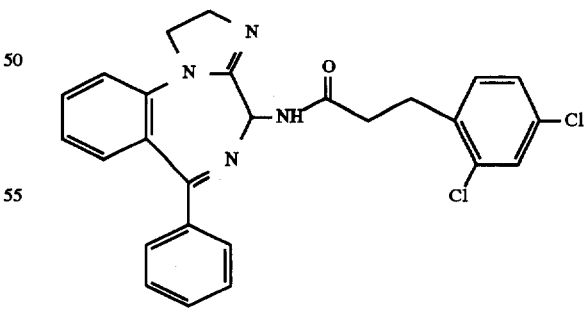

3-(2,4-Dichlorophenyl)-N-{2,4-dihydro-6-phenyl-1H-imidazo[1,2-a][1,4]benzodiazepin-4-yl}propanamide
δH(CDCl$_3$) 7.60–7.00 (13H, m), 5.85 (1H, d, J 8.1 Hz), 4.30–3.80 (4H, m), 3.15 (2H, t, J 7.7 Hz), and 2.75 (2H, t, J 7.7 Hz).

Anal. Calcd. for $C_{26}H_{22}ClN_4O \cdot H_2O$: C, 63.23; H, 4.55; N, 11.24. Found: C, 63.22; H, 4.66; N, 11.14%.

EXAMPLE 5

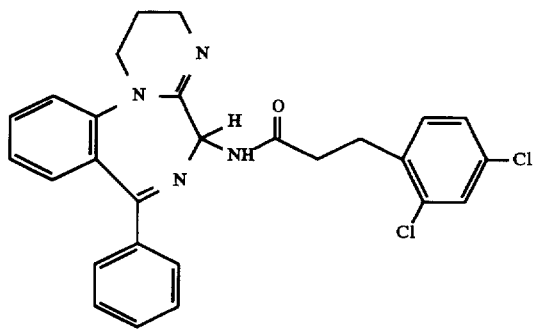

3-(2,4-Dichlorophenyl)-N-{7-phenyl- 1,2,3,5-tetrahydropyrimidino[1,2-a][1,4-]benzodiazepin-5-yl}propanamide $\delta H(CDCl_3)$ 8.00 (1H, br s), 7.60–7.05 (12H, m), 5.55 (1H, d, J 7.9 Hz), 4.00–3.40 (4H, m), 3.10 (2H, t, J 7.5 Hz), 2.70 (2H, t, J 7.5 Hz), and 2.00 (2H, m).

Anal. Calcd. for $C_{27}H_{24}Cl_2N_4O \cdot 0.2EtOAc$: C, 65.60; H, 5.07; N, 11.01. Found: C, 65.40; H, 5.01; N, 11.08%.

EXAMPLE 6

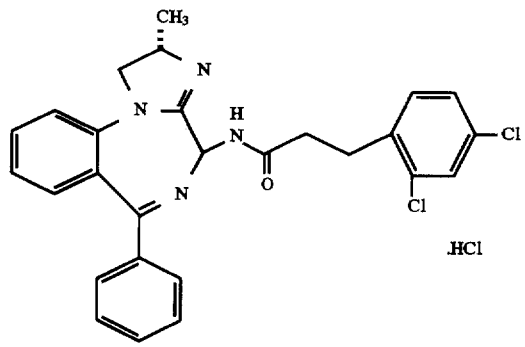

(2S)-3-(2,4-Dichlorophenyl)-N-{2,4-dihydro-2-methyl-6-phenyl-1H-imidazo[1,2-a][1,4]benzodiazepin-4-yl}propanamide hydrochloride m.p. 161°–165° C.

$\delta H(d_6$-DMSO) (Mixture of diastereoisomers) 11.8 (1H, br s), 9.70 (1H, br s), 7.85–7.35 (12H, m), 5.75 (1H, d, J 7.5 Hz), 4.60–3.90 (3H, m), 2.97 (2H, t, J 7.9 Hz), 2.70 (2H, t, J 7.9 Hz), and 1.50–1.25 (3H, m).

Anal. Calcd. for $C_{27}H_{24}Cl_2N_4O \cdot HCl \cdot H_2O$: C, 59.40; H, 4.99; N, 10.26. Found: C, 59.42; H, 4.81; N, 10.09%.

EXAMPLE 7

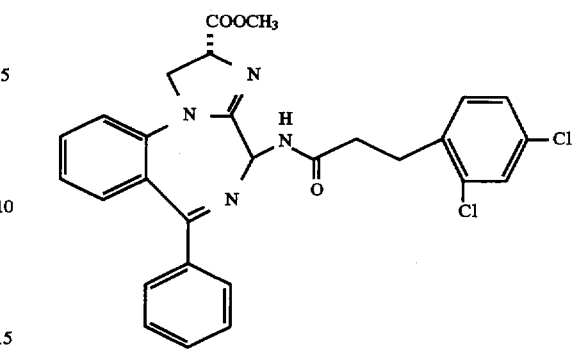

(2R)-3-(2,4-Dichlorophenyl)-N-{2,4-dihydro-2-methoxycarbonyl-6-phenyl-1H-imidazo[1,2-a][1,4]benzodiazpin-4-yl}propanamide $\delta H(CDCl_3)$ (Mixture of diastereoisomers) 7.55–7.05 (13H, m), 5.80 (1H, d, J 7.7 Hz), 4.85–3.70 (6H, m), 3.10 (2H, t, J 7.5 Hz), and 2.68 (2H, t, J 7.5 Hz).

Anal. Calcd. for $C_{28}H_{24}Cl_2N_4O_3 \cdot 0.85H_2O$: C, 61.07; H, 4.70; N, 10.17. Found: C, 61.09; H, 4.73; N, 10.16%.

EXAMPLE 8

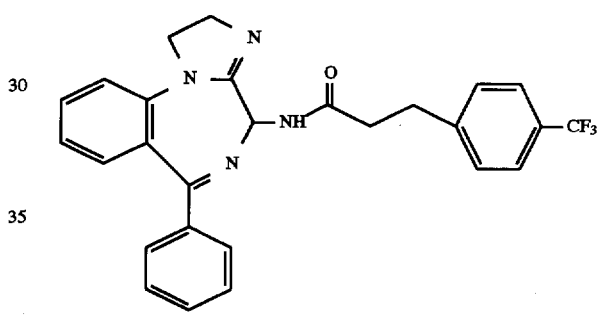

3-(4-Trifluoromethylphenyl)-N-{2,4-dihydro-6-phenyl-1H-imidazo[1,2-a][1,4]benzodiazepin-4-yl}propanamide m.p. 201°–204° C.

$\delta H(CDCl_3)$ 7.60–7.00 (14H, m), 5.85 (1H, d, J 8.1 Hz), 4.25–3.75 (4½ m), 3.10 (2H, t, J 7.7 Hz), and 2.75 (2H, t, J 7.7 Hz).

Anal. Calcd. for $C_{27}H_{23}F_3N_4O \cdot 0.25H_2O$: C, 67.42; H, 4.92; N, 11.65. Found: C, 67.38; H, 4.89; N, 11.43%.

EXAMPLE 9

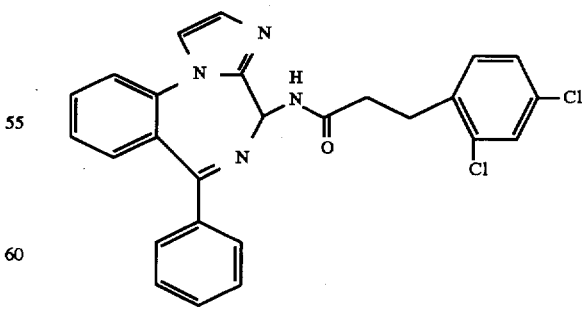

3-(2,4-Dichlorophenyl)-N-{6-phenyl-4H-imidazo[1,2-a][1,4]benzodiazepin-4-yl}propanamide A mixture of N-(2,3-dihydro-5-phenyl-2-thioxo-1H-1,4-benzodiazepin-3-yl)-3-(2,4-dichlorophenyl)propanamide (234 mg, 0.5 mmol) and 2,2-dimethoxyethylamine (210 mg, 2 mmol) in THF (6 mL) was stirred at room temperature for 17 h. Mercuric chloride (0.20 g, 0.75 mmol) was added and the mixture was stirred at 55° C. for 3 h. The solvent was evaporated under reduced pressure and the residue was dissolved in ethyl acetate (20 mL). The mixture was washed with aqueous citric acid (10%, 5 mL), brine (5 mL), saturated aqueous sodium carbonate (5 mL) and brine (5 mL), dried ($Na_2SO_4$) and the solvent was evaporated under reduced pressure to give N-[2,3-dihydro-2-(2,2-dimethoxyethylimino)-5-phenyl-1H-1,4-benzodiazepin-3-yl)-3-(2,4-dichlorophenyl)propanamide as a solid. The residue was dissolved in aqueous sulfuric acid (50%, 1 mL) and mercuric chloride (0.20 g, 0.75 mmol) was added. The mixture was stirred at room temperature for 18 h., cooled to 0° C. and the pH was adjusted to 7.0 with aqueous sodium hydroxide (10%). The mixture was extracted with ethyl acetate and the combined organic fractions were washed with water and brine, dried ($Na_2SO_4$) and the solvent was evaporated under reduced pressure. The residue was purified by flash column chromatography on silica gel, eluting with $CH_2Cl_2$/MeOH (99.5:0.5) to give 3-(2,4-dichlorophenyl)-N-{6-phenyl-4H-imidazo[1,2-a][1,4]benzodiazepin-4-yl}propanamide as a solid, m.p. 183°–184° C.

$\delta H(CDCl_3)$ 7.70–7.10 (15H, m), 6.05 (1H, d, J 8.6 Hz), 3.14 (2H, t, J 7.8 Hz), and 2.77 (2H, t, J 7.8 Hz).

Anal. Calcd. for $C_{26}H_{20}Cl_2N_4O \cdot 0.5H_2O$: C, 64.46; H, 4.37; N, 11.57. Found: C, 64.39; H, 4.16; N, 11.45%.

EXAMPLE 10

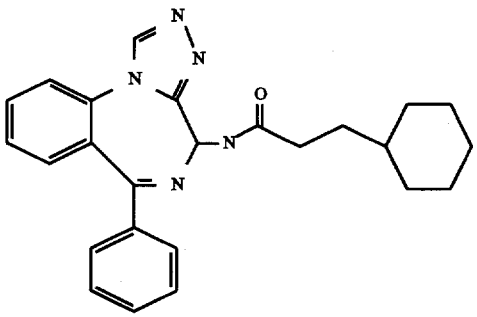

3-Cyclohexyl-N-(6-phenyl-4H-[1,2,4]triazolo[1,2,-a][1,4]benzodiazepin-4-yl)propanamide Hydrazine (157 μL, 183 mg, 5 mmol) was added to a solution of 3-cyclohexyl-N-(2,3-dihydro-1-methyl-5-phenyl-2-thioxo-1H-1,4-benzodiazepin-3-yl)propanamide (290 mg, 0.7 mmol) in THF (10 mL). The mixture was stirred at room temperature for 2 h. and the solvent was evaporated under reduced pressure. The residue was dissolved in ethanol (15 mL), triethylorthoformate (250 μL, 222 mg, 1.5 mmol) was added and the mixture was heated under reflux for 1 h. The solvent was evaporated under reduced pressure and the residue was purified by flash column chromatography on silica gel, eluting with $CHCl_3$/MeOH (96:4). The residue was recrystallized from EtOAc/Hexane to give cyclohexyl-N-(6-phenyl-4H-[1,2,4]triazolo[1,2,-a][1,4]benzodiazepin-4-yl)-propanamide as a solid (132 mg, 46%), m.p. 112°–114° C.

$\delta H(d_6$-DMSO$)$ 8.55 (1H, br d, 18.0 Hz), 7.35–6.95 (10H, m), 5.65 (1H, br d, J 8.0 Hz), 2.25 (2H, m), and 1.75–0.80 (13H, m).

Anal. Calcd. for $C_{25}H_{27}N_5O \cdot 0.75H_2O$: C, 70.31; H, 6.73; N, 16.40. Found: C, 70.61; H, 7.35; N, 16.50%.

Employing the procedure substantially as described above, but substituting N-(2,3-dihydro-5-phenyl-2-thioxo-1H-1,4-benzodiazepin-3-yl)-3-(2,4-dichlorophenyl) propanamide for the 3-cyclohexyl-N-( 2,3-dihydro-1-methyl-5-phenyl-2-thioxo-1H-1,4-benzodiazepin-3-yl) propanamide, the following compound was prepared:

EXAMPLE 11

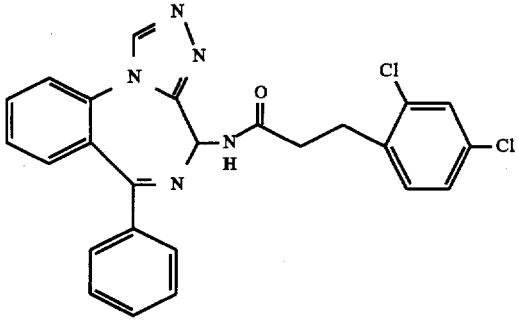

3-(2,4-Dichlorophenyl)-N-(6-phenyl-4H-[1,2,4]triazolo[1,2-a][1,4]benzodiazepin-4-yl)propanamide m.p. 105°–107° C.

$\delta H(d_6$-DMSO$)$ 8.80 (1H, br s), 7.60–6.95 (13H, m), 5.65 (1H, br s), 2.90 (2H, t, J 8.0 Hz), and 2.60 (2H, t, J 8.0 Hz).

Anal. Calcd. for $C_{25}H_{19}Cl_2N_5O \cdot H_2O$: C, 60.74; H, 4.28; N, 14.17. Found: C, 60.78; H, 5.01; N, 13.87%.

EXAMPLE 12

3-Cyclohexyl-N-{1-oxo-6-phenyl-1H, 4H-[1,2,4]oxadiazolo[4,3-a]benzodiazepin-4-yl}propanamide Step A:

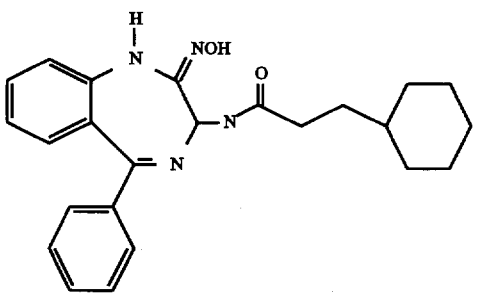

(E)- and (Z)-3-Cyclohexyl-N-(2,3-dihydro-2-hydroxyimino-5-phenyl-1H-1,4-benzodiazepin-3-yl)propanamide A mixture of 3-cyclohexyl-N-(2,3-dihydro-1-methyl-5-phenyl-2-thioxo-1H-1,4-benzodiazepin-3-yl)propanamide (740 mg, 1.83 mmol), hydroxylamine hydrochloride (140 mg, 2 mmol) and triethylamine (280 μL, 203 mg, 2 mmol) in methanol (15 mL)/THF (15 mL) was stirred at room temperature for 3 h. The solvent was evaporated under reduced pressure and the residue was purified by flash column chromatography on silica gel, eluting with $CH_2Cl_2$/MeOH (98:2). The residue recrystallized from ethyl acetate. The first isomer to crystallize was recrystallized from ethyl acetate to give (E)-3-cyclohexyl-N-(2,3-dihydro-2-hydroxyimino-5-phenyl-1H-1,4-benzodiazepin-3-yl)propanamide as a solid, m.p. 196° C.

$\delta H(d_6$-DMSO$)$ 12.20 (1H, s), 9.00 (1H, d, J 8.0 Hz), 7.70–7.30 (10H, m), 5.45 (1H, d, J 8.0 Hz), 2.30 (2H, m), and 1.80–0.75 (13H, m).

The second isomer to crystallize was recrystallized from methanol to give (Z)-3-cyclohexyl-N-(2,3-dihydro-2- hydroxyimino-5-phenyl-1H-1,4-benzodiazepin-3-yl)
propanamide as a solid, m.p. 219° C.

δH(d₆-DMSO) 9.95 (1H, s), 8.95 (1H, s), 8.75 (1H, d, J 8.0 Hz), 7.50–7.00 (9H, m), 5.70 (1H, d, J 8.0 Hz), 2.25 (2H, m), and 1.75–0.75 (13H, m).

Anal. Calcd. for $C_{24}H_{28}N_4O_2$: C, 71.26; H, 6.98; N, 13.85. Found: C, 70.89; H, 6.99; N, 13.55%.

Step B:

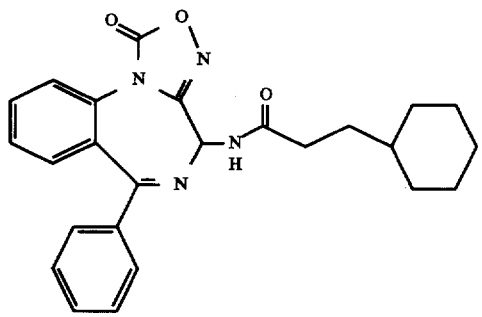

3-Cyclohexyl-N-{1-oxo-6-phenyl-1H,4H-[1,2,4]oxadiazolo[4,3-a][1,4]benzodiazepin-4-yl}propanamide Carbonyl diimidazole (35 mg, 0.21 mmol) was added to a solution of (Z)-3-cyclohexyl-N-(2,3-dihydro-2-hydroxyimino-5-phenyl-1H-1,4-benzodiazepin-3-yl) propanamide (80 mg, 0.2 mmol) in THF (15 mL) and the mixture was heated under reflux for 1 h. The solvent was evaporated under reduced pressure and the residue was triturated with ethanol (6 mL). The solid was collected and dried in vacuo to give 3-cyclohexyl-N-{1-oxo-6-phenyl-1H,4H-[1,2,4]oxadiazolo[4,3-a][1,4]benzodiazepin-4-yl}propanamide as a solid, m.p. 226° C.

δH(d₆-DMSO) 9.55 (1H, d, J 8.0 Hz), 7.95–7.35 (9H, m), 6.10 (1H, d, J 8.0 Hz), 2.30 (2H, t, J 7.0 Hz), and 1.80–0.80 (13H, m).

Anal. Calcd. for $C_{25}H_{26}N_4O_3 \cdot 0.25H_2O$: C, 69.03; H, 6.02; N, 12.88. Found: C, 68.92; H, 5.63; N, 12.67%.

EXAMPLE 13

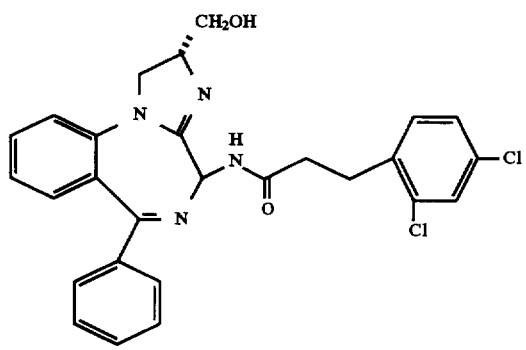

(2R)-3-(2,4-Dichlorophenyl)-N-{1,2-dihydro-2-hydroxymethyl-6-phenyl-4H-imidazo[1,2-a][1,4] benzodiazepin-4-yl}propanamide Lithium borohydride (6.5 mg, 0.3 mmol) was added to a solution of (2R)-3-(2,4-dichlorophenyl)-N-{1,2-dihydro-2-methoxycarbonyl-6-phenyl-4H-imidazo [1,2-a][1,4]benzodiazepin-4-yl}propanamide (160 mg, 0.3 mmol) in THF (20 mL) and the mixture was stirred at room temperature for 18 h. The mixture was cooled to 0° C. and methanol then water were added. The solvent was evaporated under reduced pressure, ethyl acetate was added and the mixture was washed with brine, dried (Na₂SO₄) and the solvent was evaporated under reduced pressure. The residue was purified by flash column chromatography on silica gel, eluting with $CH_2Cl_2/MeOH$ (97.5:2.5) to give (2R)-3-(2,4-dichlorophenyl)-N-{1,2-dihydro-2-hydroxymethyl-6-phenyl-4H-imidazo[1,2-a][1,4]benzodiazepin-4-yl}propanamide as a foam.

δH(CDCl₃) (Mixture of diastereoisomers) 9.20–8.30 (1H, m), 7.55–6.95 (12H, m), 5.90 (1H, m), 4.35–3.40 (6H, m), 3.10 (2H, t, J 7.5 Hz), and 2.65 (2H, t, J 7.5 Hz).

Anal. Calcd. for $C_{27}H_{24}Cl_2N_4O_2 \cdot 0.15CH_2Cl_2$: C, 62.69; H, 4.71; N, 10.77. Found: C, 62.90; H, 4.81; N, 10.67%.

EXAMPLE 14

(±)-N-[2,4-Dihydro-6-(N-methyl-N-cyclohexylamino)-1H-imidazo-[1.2a][1.4]-benzodiazepin-4-yl]-3-cyclohexylpropanamide Step A:

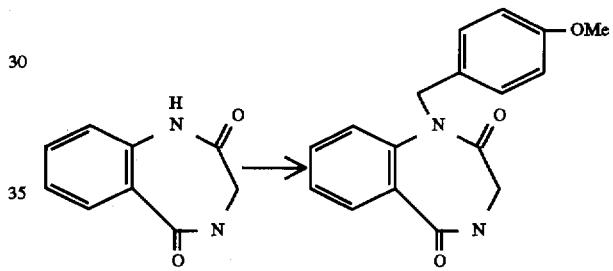

1,4-Benzodiazepine-2,5-dione (1.0 g, 5.7 mmol) was suspended in DMF (10 mL) and potassium carbonate (1.38 g, 10 mmol) added, followed by 4-methoxybenzyl chloride (0.77 mL, 5.7 mmol). The reaction mixture was stirred at room temperature under argon for 72 hours, poured into water and extracted with ethyl acetate (×3). The organic layer was washed with water and brine, dried (MgSO₄) and the solvent evaporated to give the crude product, purified by flash column chromatography affording 700 mg of product. A small sample was recrystallized from 2-propanol, (m.p. 161°–163° C.).

Step B:

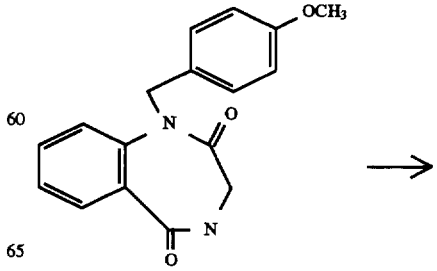

-continued

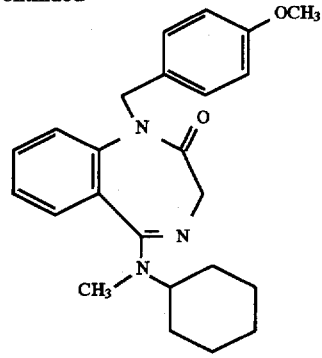

A solution of PCl$_5$ (11.6 g, 56 mmol) in 250 mL of dichloromethane was added to a stirred solution of the lactam obtained as described in Step A (15 g, 51 mmol), under argon. The reaction mixture was stirred at room temperature for 3 h, cooled to 0° C. and N-methylcyclohexylamine (39 mL, 352 mmol) added over 10 min. The reaction mixture was warmed to room temperature, stirred for 2 h, poured into saturated sodium bicarbonate, partitioned and the organic phase dried (MgSO$_4$) and the solvent evaporated. Purification by flash column chromatography afforded 17 g of the amidine used in the next step.

Step C:

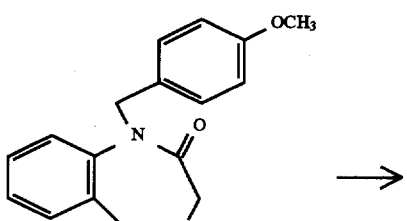

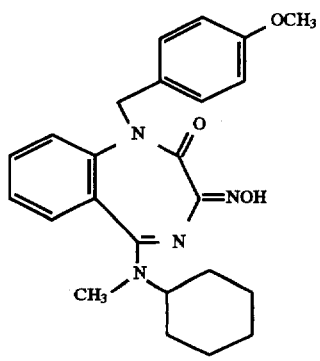

The amidine obtained in Step B (16 g, 41 mmol) in 50 mL of toluene was added to a cooled (−30° C.) and stirred suspension of potassium t-butoxide (11.5 g, 102 mmol) in 400 mL of toluene. After 30 min, isoamyl nitrite (8 mL, 76 mmol) was added and the reaction mixture stirred for 1 h at −20° to −30° C. This was then poured into 10% citric acid solution/ethyl acetate, stirred for 10 min and the pH adjusted to 8 with potassium carbonate solution. The phases were separated and the organic phase washed with water, saturated sodium bicarbonate solution and brine. The aqueous phases were back extracted with ethyl acetate and the combined phases dried (MgSO$_4$) and the solvent evaporated to give 13 g of oxime used in the next step without further purification.

Step D:

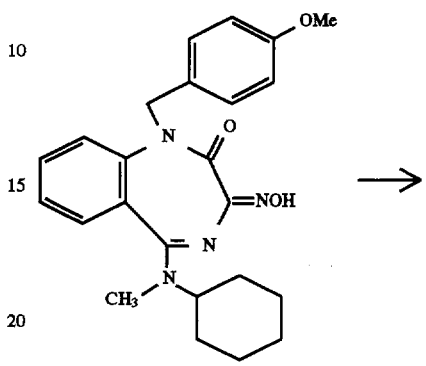

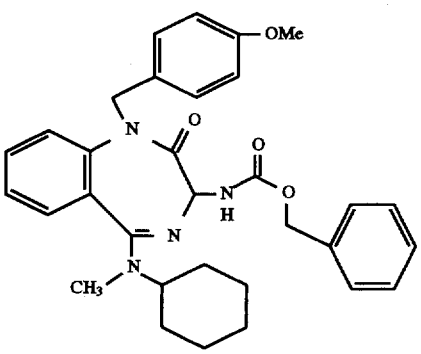

A solution of the oxime (13 g, 31 mmol) in THF (250 mL) was treated with triethylamine (6.5 mL, 47 mmol) and ethyl isocyanate (3.7 mL, 47 mmol). The reaction mixture was heated to 60° C. for 3 hours, cooled to room temperature, the volatiles evaporated and the residue purified by flash column chromatography on silica to afford 8 g of oxime carbamate. 7 g of this material was dissolved in methanol and hydrogenated at 50 psi over 2 g of 10% palladium/charcoal catalyst for 3 hours. The mixture was then filtered through celite, washing solid residues well with methanol. The combined filtrates were evaporated and the resulting oil dissolved in 150 mL THF. To the rapidly stirred and cooled (0° C.) solution were added water (100 mL), saturated NaHCO$_3$ (100 ml) and benzyl chloroformate (2.15 mL, 15 mmOD. The pH of the reaction mixture was maintained at 8–9 by addition of 1M NaOH. After 1 hour, the reaction mixture was poured into brine and extracted with ethyl acetate (×2). The organic phases were washed with water and brine, dried (MgSO$_4$) and solvent evaporated. The crude product was purified by flash column chromatography to give 5.5 g of pure material.

NMR (300 MHz, CDCl$_3$) δ: 7.1–7.5 (m, 9H), 7.03 (brd, J=8.7 Hz, 2H), 6.68 (d, J=8.8 Hz, 2H), 6.3 (brs, 1H), 5.63 (d, J=14.6 Hz, 1H), 5.1 (s, 2H), 5.05 (d, J=8.3 Hz, 1H), 4.56)brd, J=14.6 Hz, 1H), 3.7 (s, 3H), 2–2.3 (brs, 4H), 0.8–1.8 (m, 10H).

Step E:

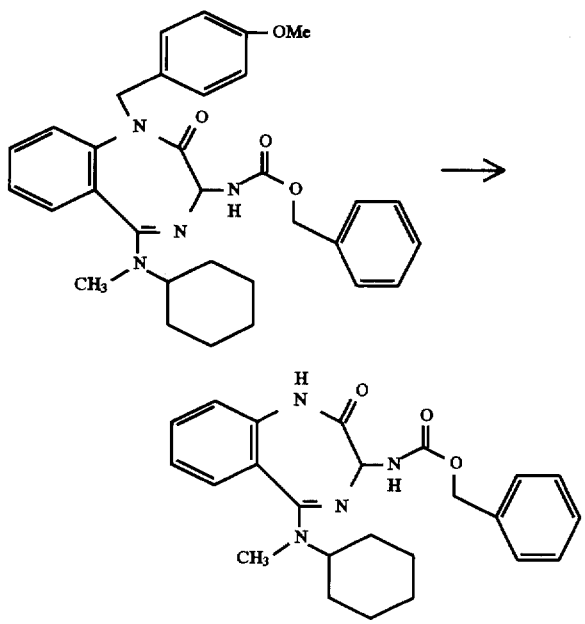

The lactam (1.0 g, 1.9 mmol) was dissolved in acetonitrile (6 mL) and water (2 mL) added, followed by ceric ammonium nitrate (5.2 g). Reaction mixture stirred at room temperature for 2 hours, poured into saturated potassium sodium tartrate solution and extracted with ethyl acetate. The organic phase was washed with water and brine and the aqueous phases back extracted with ethyl acetate. The combined extracts were dried ($MgSO_4$) and solvent evaporated to give the crude product purified by flash column chromatography in silica. Yield 600 mg.

NMR (300 MHz, $CDCl_3$) δ: 9.25 (brs, 1H), 7.1–7.6 (m, 9H), 6.3 (brs, 1H), 5.1–5.2 (m, 3H), 3.1–3.4 (m, 1H), 2.8 (brs, 3H), 0.8–2 (m, 10H).

Step F:

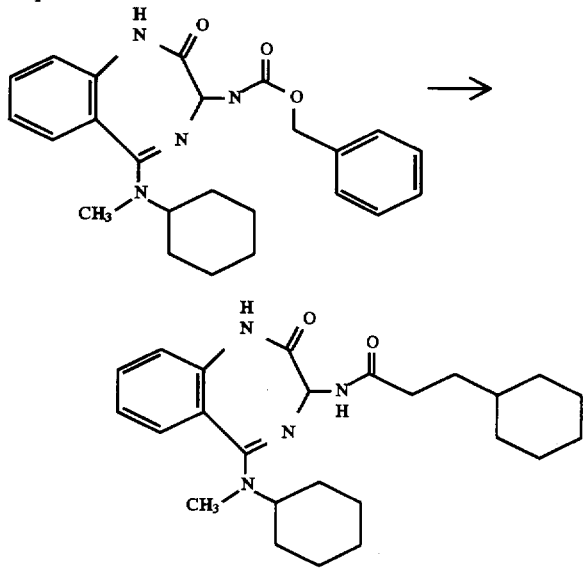

The lactam (500 mg, 1.2 mmol) and Lawesson's reagent (530 mg, 1.3 mmol) in toluene (25 ml) were heated to 100° C. for 3 hours. The reaction mixture was cooled to room temperature and volatiles evaporated. Resulting solid dissolved in 5 ml DCM and 30% HBr/HOAc (6 ml) added. The reaction mixture was stirred for 3 hours, ether (approx. 50 mL) added and the precipitate filtered off under argon, washed with ether and dried. The solid obtained (210 mg) was added to a mixture of cyclohexanepropionic acid (150 mg, 1 mmol), HOBt (135 mg, i mmol), triethylamine (280 ml, 2 mmol) and EDC (180 mg, 1 mmol) in DMF (2 mL). The reaction mixture was stirred for 30 minutes, poured into water and extracted with ethyl acetate. The organic layer was washed with water, saturated $NaHCO_3$ and brine and the aqueous phases back extracted with ethyl acetate. The combined organic phases were dried ($MgSO_4$) and solvent evaporated to give the product purified by flash chromatography. Yield 170 mg.

NMR (300 MHz, $CD_3OD$) δ: 7.5–7.85 (m, 2H), 7.2–7.4 (m, 2H), 5.25 (s, 1H), 3.2–3.45 (m, 1H), 2.75 (s, 3H), 2.2–2.45 (m, 2H), 0.8–2.0 (m, 23H).

Step G:

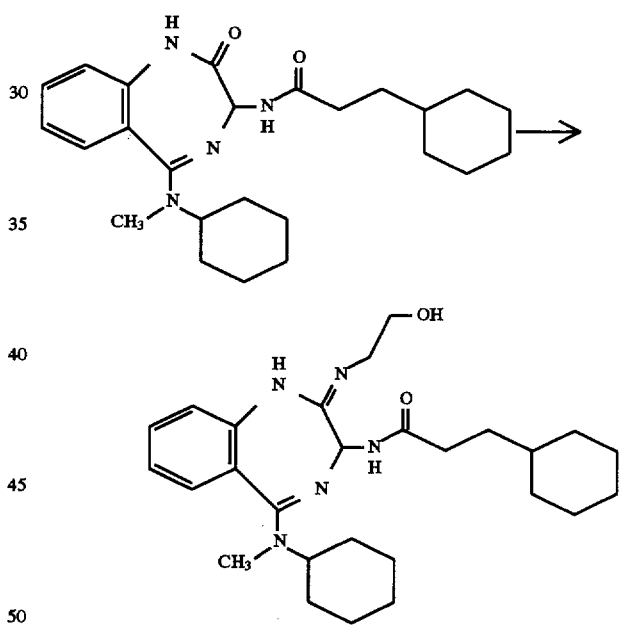

The thioamide (87 mg, 0.2 mmol) was dissolved in THF (3 mL) and ethanolamine (60 μL, 1 mmol) added, followed by mercuric chloride (81 mg, 0.3 mmol). The reaction mixture was stirred at room temperature for 5 hours, poured into saturated $NaHCO_3$ solution and extracted with ethyl acetate. The organic layer was washed with water, brine, dried ($MgSO_4$) and solvent evaporated. Crude product was purified by flash column chromatography to afford 55 mg of product.

NMR (300 MHz, $CD_3OD$): 7.45 (dd, J=7.8, 1.5 Hz, 1H), 7.4 (m, 1H), 7.16 (dd, J=8.3, 1.0 Hz, 1H), 7.04 (m, 1H), 4.94 (s, 1H), 3.6–3.75 (m, 2H), 3.41 (t, J=5.1 Hz, 2H), 3.2–3.5 (m, 1H), 2.76 (s, 3H), 2.33 (m, 2H), 0.8–2.0 (m, 23H).

Step H:

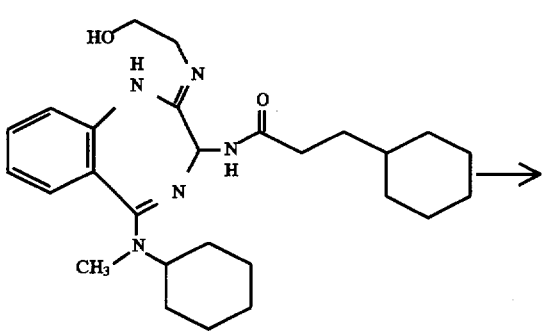

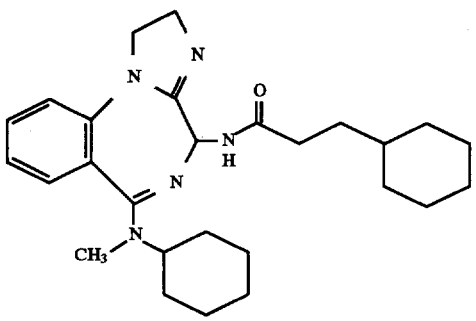

To a cooled (0° C.) solution of the alcohol (54 mg, 0.11 mmol) in dichloromethane (5 mL) was added diisopropylethylamine (44 µL, 0.25 mmol) followed by methanesulfonyl chloride (9 µL, 0.12 mmol). The reaction mixture was stirred at 0° C. for 30 minutes, then room temperature for 2 hours, poured into water and extracted with ethyl acetate. The organic phase was washed with water, saturated NaHCO$_3$ and brine, the aqueous phases back extracted with ethyl acetate and the combined extracts dried (MgSO$_4$) and solvent evaporated. The solid obtained was recrystallized from ethyl acetate/hexane to afford (±)-N-[2,4-Dihydro-6-(N-methyl-N-cyclohexylamino)-1H-imidazo[1.2a][1,4]-benzodiazepin-4-yl]-3-cyclohexylpropanamide.

Yield 29 mg, m.p. 195°–196° C.

NMR (300 MHz, DMSO): 8.44 (d, J=8.5 Hz, 1H), 7.48 (m, 1H), 7.4. (d, J=8.1 Hz, 1H), 7.1–7.2 (m, 2H), 5.26 (d, J=8.8 Hz, 1H), 3.4–4.0 (m, 4H), 2.6 (brs, 3H), 2.15 (m, 2H), 0.7–1.9 (m, 23H). δH(DMSO).

EXAMPLE 15

(+)-3-(2,4-Dichlorophenyl)-N-[2,4-dihydro-2(S)-methyl-6-isopropyl-1H-imidazo[1.2a][1,4]benzodiazepin-4-yl] propanamide and (−)-3-(2,4-Dichlorophenyl)-N-[2,4-dihydro-2(S)-methyl-6-isopropyl-1H-imidazo-[1.2a][1,4] benzodiazepin-4-yl]propanamide Step A:

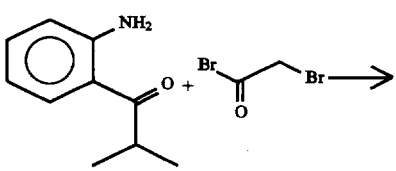

-continued

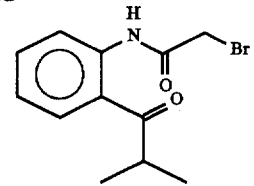

To a solution of 2-amino isopropiophenone (15.0 g, 92 mmol) in methylene chloride (240 mL) at 0° C. under argon was added bromoacetyl bromide (9.05 mL, 104 mmol) followed by 3N NaOH (92 mL). The reaction was stirred at room temperature for 1 hr or until complete. The pH was adjusted to 6 with 1N HCl and methylene chloride layer removed. The aqueous extract was washed with methylene chloride (100 mL) and the combined organic extracts washed with 5% sodium biocarbonate, dried (MgSO$_4$), filtered and concentrated to an oil (yield 24.1 gms. 92%).

$^1$H NMR (CDCl$_3$) δ 1.22 (d, 6H), 3.65 (septet, 1H), 4.0 (s, 2H), 7.2 (dt, 1H), 7.58 (dt, 1H), 7.06 (dd, 1H), 8.71 (dd, 1H).

Step B:

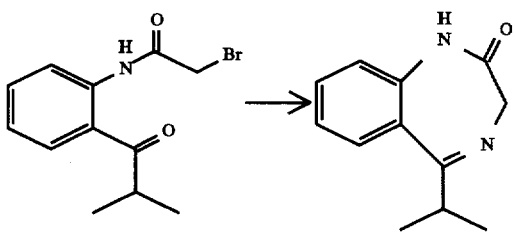

Ammonia was bubbled through ice-cooled ethanol (70 mL) for 10 min., then 2-bromo-N-[2-(2-methylpropanoyl) phenyl]acetamide (1.99 g, 7 mmol) was added. The mixture was stirred at room temperature for 18 h., then the solvent was evaporated under reduced pressure. Aqueous hydrochloric acid (1M, 50 mL). The pH was adjusted to 10.0 with aqueous sodium hydroxide (5M) and the mixture was extracted with methylene chloride (3×30 mL). The combined organic fractions were dried (Na$_2$SO$_4$) and the solvent was evaporated under reduced pressure to give 2,3-dihydro-5-(1-methylethyl)-1H-1,4-benzodiazepin-2-one (1.32 g, 93%) as a colorless solid.

$^1$H NMR (CDCl$_3$): δ 8.73 (1H, br s), 7.58 (1H, d, J 7.9 Hz), 7.45 (1H, t, J 7.9 Hz), 7.22 (1H, t, J 7.9 Hz), 7.08 (1H, d, J 7.9 Hz), 4.13 (2H, br s), 3.16 (1H, septet, J 6.7 Hz), and 1.13 (6H, d, J 6.7 Hz).

Step C:

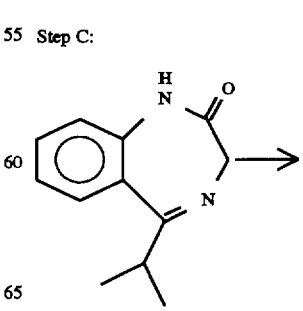

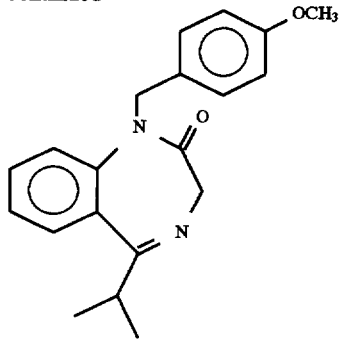

To a solution of the isopropyl benzodiazepine (6.0 g, 30 mmol) and p-methoxybenzyl chloride (5.2 g, 3.26) in DMF (60 mL) was added potassium carbonate (8.2 g, 60 mmol) and the mixture warmed to 60° C. for 3.0 hrs. The reaction was quenched into water (200 mL) and ethyl acetate (300 mL) and the organic layer removed. The aqueous layer was washed with ethyl acetate (200 mL) and the combined organic layers washed with water (100 mL) and brine (50 mL). The organic extracts were dried (Na₂SO₄), filtered and concentrated to give a white solid. The solid was triturated with hexanes to give, upon filtration, 9.0 gms, 94% of product.

¹H NMR (CDCl₃): δ 50.7 (d, 2H), 1.15 (d, 2H), 3.05 (Septet, 1H), 3.65 (d, 1H), 3.75 (s, 3H), 4.65 (d, 1H), 4.72 (d, 1H), 5.45 (d, 1H), 6.72 (d, 2H), 7.02 (d, 2H), 7.2 (dt, 1H), 7.3–7.5 (m, 3H).

Step D:

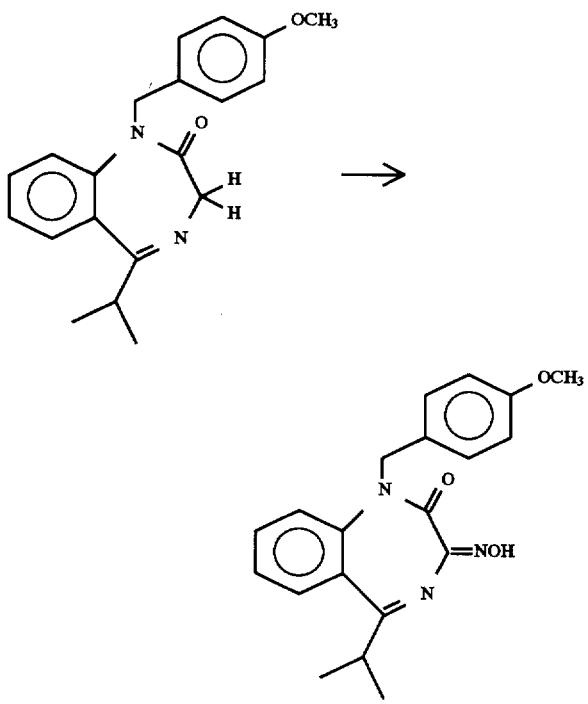

To the p-methoxybenzylbenzodiazepine (4.5 g, 14.0 m) in toluene (180 mL) at −78° C. under agon was added potas- sium hexamethyldisilazide (0.5M in toluene) (56.0 mL, 28.0 mmol). The dark yellow/orange solution was stirred at −78° C. for 15 min., and then isoamyl nitrite (3.0 mL, 21 mmol) slowly added. The reaction was allowed to stir for 30 minutes, quenched into 10% aq. sodium bicarbonate and product extracted into ethyl acetate (300 mL). The organic extract was dried (Na₂SO₄) and concentrated to an oil (4.9 g). Chromatography on silica (1:1 ethyl acetate/hexane) gave 3.0 g (61%) of pure product.

¹H NMR(CDCl₃): δ 0.8 (d, 2H), 1.3 (d, 2H), 3.2 (Septet, 1H), 3.7 (s, 3H), 4.8 (d, 1H), 5.5 (d, 1H), 6.8–8.0 (m, 9H).

Step E:

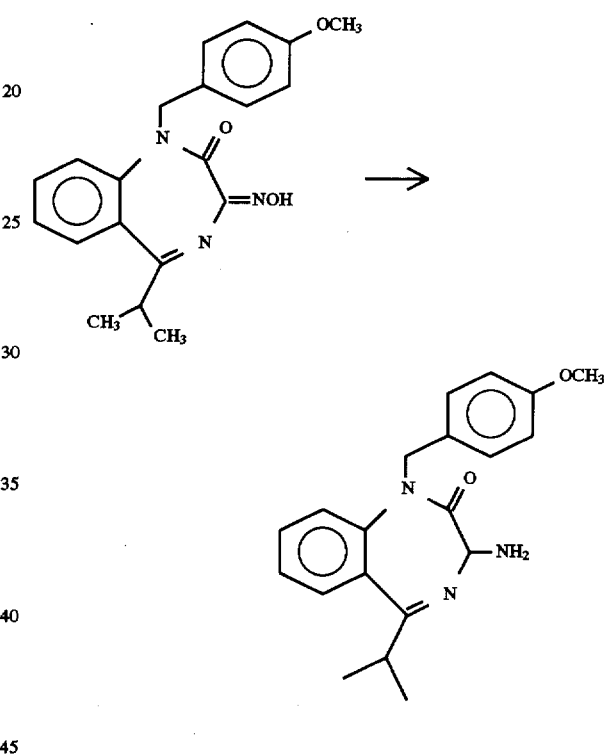

The oxime (2.8 gms, 8 mmol) was dissolved in acetic acid (225 mL) and 10% Pd/C (1.12 gms) added. The mixture was stirred rapidly under 1 atmosphere of hydrogen for 90 min or until complete by HPLC. The reaction was filtered, the catalyst washed with methylene chloride (200 mL) and the filtrates concentrated in vacuo to an oil. The oil was dissolved in saturated aqueous sodium bicarbonate (100 mL) and product extracted with ethyl acetate (3×150 mLs). Concentration of the dried (Na₂SO₄) extracts gave 2.60 gms (97%).

¹H NMR(CDCl₃): δ 0.6 (d, 3H), 1.25 (d, 2H), 3.0 (brm, 3H), 3.75 (s, 3H), 4.4 (s, 1H), 4.75 (d, 1H), 5.45 (d, 1H), 6.7 (d, 2H), 7.05 (d, 2H), 7.20 (dt, 1H), 7.4–7.5 (m, 3H).

Step F:

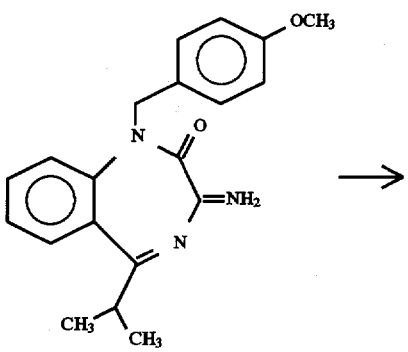

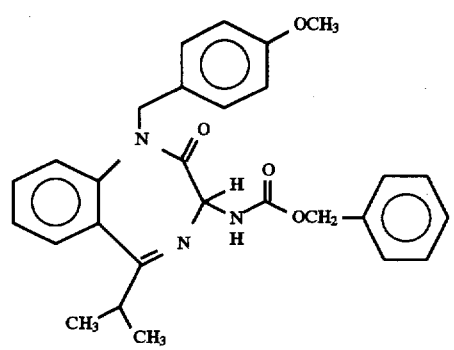

To a solution of the amine (5.58 g, 16.5 mmol) in THF (200 mL) at 0° C. was added sat. aqueous sodium bicarbonate (135 mL). The mixture was stirred well as benzyl chloroformate (2.84 mL, 18.2 mmol) was slowly added. The reaction was complete after 15 mins. and was quenched by addition of ethyl acetate (400 mL) and H$_2$O (50 mL). The organic layer was removed and the aqueous layer washed with ethyl acetate (100 mL). The organic extracts were combined, dried (Na$_2$SO$_4$), filtered and concentrated to an oil (7.6 g 98%).

$^1$H NMR(CDCl$_3$): δ 0.60 (d, 3H), 1.60 (d, 3H), 3.0 (Septet, 1H), 3.70 (s, 3H), 4.75 (d, 1H), 5.10 (s, 2H), 5.20 (d, 1H), 5.45 (d, 1H), 6.6 (d, 1H), 6.70 (d, 2H), 7.0 (d, 2H), 7.2–7.6 (m, 9H).

Step G:

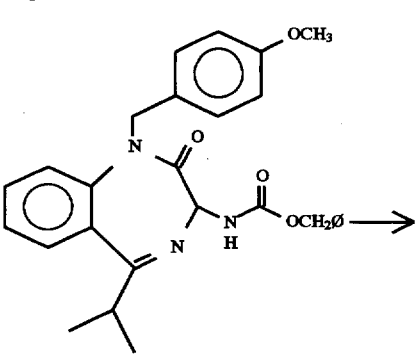

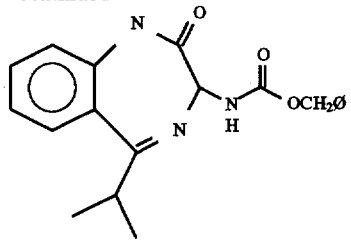

To a solution of the carbamate (7.6 g, 16.1 mmol) in 33% aqueous acetonitrile (51 mL) was added cerric ammonium nitrate (43.4 g, 80.5 mmol) as a solid and the mixture allowed to stir for 30 min or until the reaction was complete. The reaction was poured into an aqueous solution of Rochelles salt (380 mL) and allowed to stir for ½ hr. The product was extracted with ethyl acetate (3×300 mL), dried (Na$_2$SO$_4$), filtered and concentrated to an oil (7.8 g). Flash column chromatography on silica (30%, ethyl acetate/hexane) gave 4.56 g (81%) of product.

$^1$H NMR (CDCl$_3$): δ 0.92 (d, 3H), 1.25 (d, 3H), 3.15 (Septet, 1H), 5.10 (s, 2H), 5.18 (d, 1H), 6.42 (d, 1H), 7.0–7.6 (m, 9H), 8.8 (brs, 1H).

Step H:

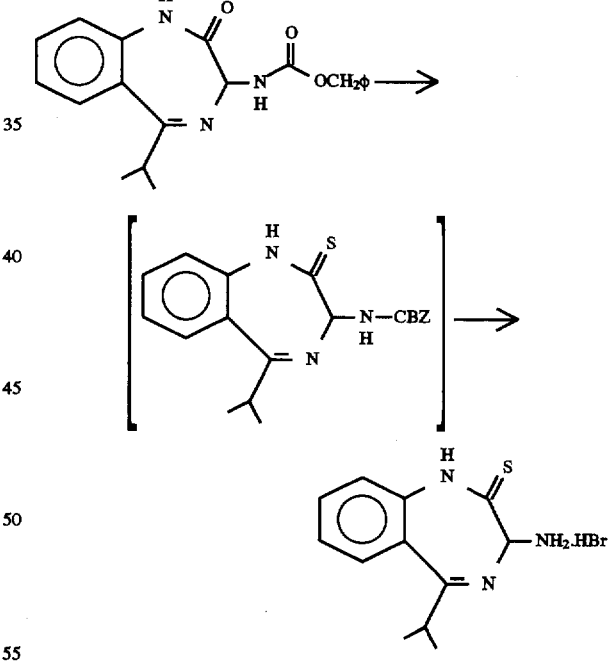

To a solution of the carbamate (2.5 g, 7.1 mmol) in toluene (200 mL) was added Lawessons reagent (3.45 g, 8.54 mmol) and the reaction warmed to 100° C. for 1½ hrs. The reaction was cooled, concentrated and resulting oil dissolved in methylene chloride (40 mL). A solution of 30% HBr/acetic acid (20 mL) was added and the reaction stirred for 1½ hrs. The reaction was diluted with ether (200 mL), filtered under argon, and the solid washed with ether to give 3.0 gms. of material (130%). This material was used as is as soon as possible.

Step I:

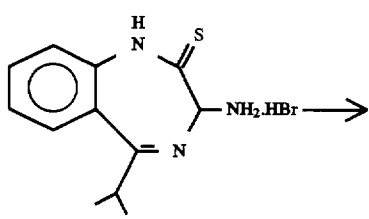

To a mixture of 3-(2,4-dichlorophenyl)propionic acid (2.02 g, 9.22 mmol) 1-hydroxybenzotriazole hydrate (1.24 g, 9.22 mmol), triethylamine (2.48 mL, 17.8 mmol) and EDC (1.92 g, 10 mmol) in DMF (55 mL) was added the amine hydrobromide (3.0 g crude, 7.1 mmol). The reaction was stirred for 1 hr and quenched by addition of 5% citric acid (25 mL). The product was extracted into ethyl acetate (3×250 mL) and the extracts washed with 5% citric acid (25 mL), H$_2$O (25 mL) and 5% sodium bicarbonate (2×25 mL). The organic extracts were dried (Na$_2$SO$_4$), filtered and concentrated to an oil (3.2 g). Flash column chromatography on silica (1:1 ethyl acetate/hexane) gave 1.95 g (63 %) of product.

$^1$H NMR (CDCl$_3$): δ 0.98 (d, 3H), 1.30 (d, 2H), 2.70 (t, 2H), 3.10 (t, 2H), 3.18 (Septet, 1H), 5.55 (d, 1H), 7.0–7.8 (m, 8H), 9.9 (brs, 1H).

Step J:

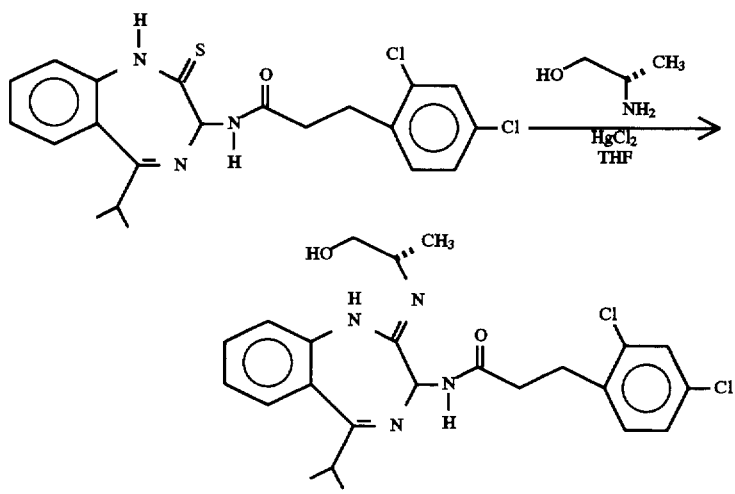

To a solution of the thiolactam (1.0 g, 2.30 mmol) and S(+)-2-amino-1-propanol (0.90 mL, 11.5 mmol) in THF (40 mL) was added HgCl$_2$ (0.94 g, 3.45 mmol). The reaction was stirred for 6 hrs at 50° C. and then at RT for 18 hrs. The reaction was concentrated and oil chromatographed on silica (70% ethyl acetate/hexane) to give 1.07 gms (98%) of product.

$^1$H NMR (CDCl$_3$): δ 0.85 (dd, 3H), 1.15 (t, 2H), 1.22 (d, 3H), 2.68 (t, 2H), 3.04.0 (m, 7H), 4.90 (dd, 1H), 6.55 (m, 1H), 7.05 (t, 1H), 7.1–7.5 (m, 6H).

Step K:

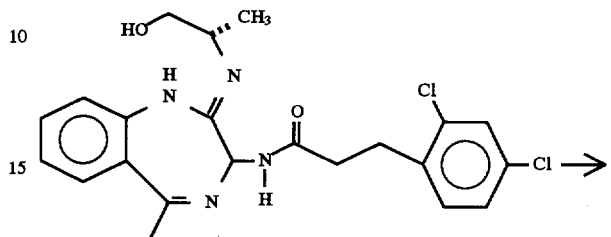

To a solution of the amidine-alcohol (1.07 g, 2.25 mmol) in methylene chloride (20mL) containing diisopropylethylamine (1.0 mL, 5.63 mmol) at 0° C. was added methanesulfonyl chloride (0.184 mL, 2.36 mmol). The reaction was allowed to stir at room temperature for 1 hr and then quenched by addition of aqueous saturated sodium bicarbonate (20 mL). The product was extracted with CH$_2$Cl$_2$ (3×50 mL) dried (Na$_2$SO$_4$) and concentrated to a foam. The crude solid was chromatographed on silica using 100% ethyl acetate to give 0.40 g (−)-3-(2,4-dichlorophenyl)-N-[2,4-dihydro-2(S)-methyl-6-isopropyl-1H-imidazo[1,2a][1,4]

benzodiazepin-4-yl]propanamide, followed by methanol/ methylene chloride/aq NH₄OH (5/95/1) to give 0.464 g (+)-3-(2,4-Dichlorophenyl)-N-[2,4-dihydro-2(S)-methyl-6-isopropyl-1H-imidazo[1,2a][1,4]benzodiazepin-4-yl] propanamide after concentration of fractions. Both isomers were precipitated as their hydrochloride salts from ethyl acetate (25 mg/mL) upon addition of anhyrous HCl gas to the solutions. Filtration gave both pure (−)-3-(2,4-dichlorophenyl)-N-[2,4-dihydro-2(S)-methyl-6-isopropyl-1H-imidazo[1,2a][1,4]benzodiazepin-4-yl]propanamide, hydrochloride (330 mg), and (+)-3-(2,4-Dichlorophenyl)-N-[2,4-dihydro-2(S)-methyl-6-isopropyl-1H-imidazo[1,2a][1,4]benzodiazepin-4-yl]propanamide (350 mg).

(−)-3-(2,4-dichlorophenyl)-N-[2,4-dihydro-2(S)-methyl-6-isopropyl-1H-imidazo[1,2a][1,4]benzodiazepin-4-yl] propanamide m.p. 187°–188° C.

$[\alpha]^D \text{MeOH} = -168.4°$ $^1$NMR(CD$_3$OD) δ: 0.92 (d,3H), 1.30 (d, 3H), 1.55 (d,3H), 2.72 (d,t,2H), 3.05 (d,t,2H),3.30 (m, 1H), 4.35 (m, 1H), 4.5–4.6(m, 2H), 5.50 (S,1H), 7.2–8.0 (m,7H).

(+)-3-(2,4-Dichlorophenyl)-N-[2,4-dihydro-2(S)-methyl-6-isopropyl-1H-imidazo[1,2a][1,4]benzodiazepin-4-yl] propanamide m.p. 95°–100° C.

$[\alpha]^D \text{MeOH} = +87.8°$ $^1$NMR(CD$_3$OD) δ: 0.92 (d,3H), 1.32 (d, 3H), 1.34 (d,3H), 2.72 (d,t,2H), 3.05 (d,t,2H),3.30 (m, 1H), 3.90 (d, d,1H), 4.52 (m, 1H), 5.0 (t, 1H), 5.50 (S,1H), 7.2–8.0 (m,7H).

The following compounds were prepared in a similar manner as described in Example 15 for the preparation of (−)-3-(2,4-dichlorophenyl)-N-[2,4-dihydro-2(S)-methyl-6-isopropyl-1H-imidazo[1,2a][1,4 ]benzodiazepin-4-yl] propanamide, and (+)-3-(2,4-Dichlorophenyl)-N-[2,4-dihydro-2(S)-methyl-6-isopropyl-1H-imidazo[1,2a][1,4] benzodiazepin-4-yl]propanamide by reaction of the aminothiolactam described above with the appropriate acid and amino alcohol.

EXAMPLE 16

(+)-3-(2,4-Dichlorophenyl)-N-[2,4-dihydro-1(R)-methyl-6-isopropyl-1H-imidazo[1,2a][1,4]benzodiazepin-4-yl] propanamide m.p. 75°–80° C.

$[\alpha]^D \text{MeOH} = +174.5°$ $^1$NMR(CDCl$_3$) δ: 0.88 (d,3H), 1.24 (d, 3H), 1.50 (d,3H), 2.65 (t,2H), 3.05 (m, 1H), 3.08 (t,3H), 3.42 (dd, 1H), 3.85 (dd, 1H), 4.18 (m, 1H), 5.74 (d,1H), 7.0–7.5 (m,8H).

EXAMPLE 17

(−)-3-(2,4-Dichlorophenyl)-N-[2,4-dihydro-1(R)-methyl-6-isopropyl-1H-imidazo[1,2a][1,4]benzodiazepin-4-yl] propanamide m.p. 103°–105° C.

$[\alpha]^D \text{MeOH} = -63°$ $^1$NMR(CDCl$_3$) δ: 0.88 (d,3H), 1.24 (d, 3H), 1.28 (d,3H), 2.64 (t,2H), 3.05 (m, 1H), 3.05 (t,2H), 3.42 (dd, 1H), 4.14 (dd, 1H), 4.58 (m, 1H), 6.95 (d,1H), 7.0–7.5 (m,7H).

EXAMPLE 18

(±)-3-(2,4-Dichlorophenyl)-N -[2,4-dihydro-6-isopropyl-1H -imidazo-[1.2a][1,4]benzodiazepin-4-yl]propanamide

78°–180° C.

$^1$NMR(CDCl$_3$) δ: 0.9 (d,3H), 1.25 (d, 3H), 2.70 (t,2H), 3.04 (Sept, 1H), 3.06 (t,2H), 3.6–4.2 (m,4H), 5.76 (d, 1H), 6.98 (d,1H), 7.1–7.4 (m, 4H), 7.45 (t, 1H), 7.52 (dd, 1H).

EXAMPLE 19

(−)-3-(2,4-Dichlorophenyl)-N-[2,4-dihydro-1(S)-methyl-6-isopropyl-1H-imidazo[1,2a][1,4]benzodiazepin-4-yl] propanamide

82°–85° C.

$[\alpha]^D \text{MeOH} = -185.9°$ $^1$NMR(CDCl$_3$) δ: 0.87 (d,3H), 1.24 (d, 3H), 1.50 (d,3H), 2.65 (t,2H), 3.05 (m, 1H), 3.06 (t,3H), 3.45 (dd, 1H), 3.85 (dd, 1H), 4.18 (m, 1H), 5.77 (d,1H), 7.0–7.5 (m,8H).

EXAMPLE 20

(+)-3-(2,4-Dichlorophenyl)-N-[2,4-dihydro-1(S)-methyl-6-isopropyl-1H-imidazo[1,2a][1,4]benzodiazepin-4-yl] propanamide

138°–140° C.

$[\alpha]^D \text{MeOH} = +66.4°$ $^1$NMR(CDCl$_3$) δ: 0.88 (d,3H), 1.24 (d, 3H), 1.27 (d,3H), 2.64 (t,2H), 3.05 (t,2H), 3.05 (m, 1H), 3.42 (dd, 1H), 4.12 (m, 1H), 4.60 (m, 1H), 5.60 (d,1H), 6.98 (d, 1H), 7.0–7.5 (m,7H).

What is claimed is:

1. A compound of structural formula:

the individual diastereomers, enantiomers and mixtures thereof or a pharmaceutically acceptable salt thereof, wherein A is a 2 or 3 membered chain which is all carbon or one and only one member can be nitrogen or oxygen, which is unsubstituted or substituted on carbon with
   $C_{1-3}$ alkyl either unsubstituted or substituted with hydroxy,
   $C_{1-3}$ alkoxycarbonyl or
   3) oxo;

Z is
   1) $C_{2-3}$ alkenylene; or
   2) 2- or 3-membered saturated chain, either all carbon or including not more than one heteroatom selected from —NH—, or —S—;

$R^1$ is
   1) $C_{5-7}$ cycloalkyl,
   2) phenyl, either unsubstituted or substituted with up to 2 substituents selected from Cl, Br, I, F, CF$_3$ or $C_{1-3}$ alkyl;

$R^2$ is
   1) phenyl,
   —NR$^3$R$^4$, wherein R$^3$ and R$^4$ an independently $C_{1-3}$ alkyl or $C_{5-7}$ cycloalkyl,
   3) $C_{1-5}$ alkyl or
   4) $C_{5-6}$ cycloalkyl.

2. The compound of claim 1 selected from the group depicted in the following Table.

31

[Structure: benzodiazepine-type compound with A bridge between two N atoms, amide linkage to -(CH2)3-R¹, and =N-R² imine group]

| A | R¹ | R² |
|---|----|----|
| [CH2-CH2] (2-membered) | cyclohexyl | Ph |
| [CH2-CH2-CH2] (3-membered) | cyclohexyl | Ph |
| [CH(CH3)-CH2] with CH3 wedge | cyclohexyl | Ph |
| [CH2-CH2] | 2,4-di Cl Ph | Ph |
| [CH2-CH2-CH2] | 2,4-di Cl Ph | Ph |
| [CH(CH3)-CH2] with CH3 wedge | 2,4-di Cl Ph | Ph |
| [CH(COOCH3)-CH2] with COOCH3 wedge | 2,4-di Cl Ph | Ph |
| [CH2-CH2] | 4-CF₃Ph | Ph |
| [CH=CH] | 2,4-di Cl Ph | Ph |
| [CH=N-] | cyclohexyl | Ph |
| [CH=N-] | 2,4-di Cl Ph | Ph |
| [CH(CH3)-CH2] with CH3 | 2,4-di Cl Ph | i Pr |
| [CH(CH3)-CH2] with CH3 dashed | 2,4-di Cl Ph | i Pr |
| [CH2-CH2] | 2,4-di Cl Ph | i Pr |
| [CH(CH3)-CH2] with H3C wedge | 2,4-di Cl Ph | i Pr |
| [C(=O)-O-] | cyclohexyl | Ph |

-continued

| A | R¹ | R² |
|---|----|----|
| [CH(CH2OH)-CH2] with CH2OH dashed | 2,4-di Cl Ph | Ph |
| [CH2-CH2] | cyclohexyl | -N(CH3)(cyclohexyl) |
| [CH(CH3)-CH2] with CH3 dashed | cyclohexyl | Ph. |

3. A pharmaceutical formulation comprising a pharmaceutically acceptable carrier and an effective antiarrhythmic amount of the compound of claim 1.

4. The pharmaceutical formulation of claim 3 comprising a pharmaceutical carrier and an effective amount of the compound of claim 1 in combination with another antiarrhythmic or cardiovascular agent.

5. A method for the prevention or treatment of arrhythmia which comprises the administration to a patient in need of such treatment of an effective amount of the compound of claim 1.

6. The method of claim 5 wherein the compound of claim 1 is administered in combination with another antiarrhythmic or cardiovascular agent.

7. A method for the prevention or treatment of arrhythmia which comprises the administration to a patient in need of such treatment of an effective mount of a compound of structural formula:

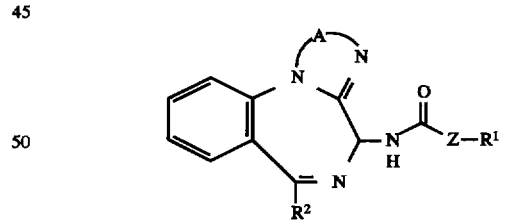

the individual diastereomers, enantiomers and mixtures thereof or a pharmaceutically acceptable salt thereof, wherein A is a 2 or 3 membered chain which is all carbon or one and only one member can be nitrogen or oxygen, which is unsubstituted or substituted on carbon with
 1) $C_{1-3}$ alkyl either unsubstituted or substituted with hydroxy,
 2) $C_{1-3}$ alkoxycarbonyl or
 3) oxo;

Z is
 1) $C_{2-3}$ alkenylene; or 2) 2- or 3-membered saturated chain, either all carbon or including not more than one heteroatom selected from —NH—, or —S—;

$R^1$ is
1) $C_{5-7}$ cycloalkyl,
2) phenyl, either unsubstituted or substituted with up to 2 substituents selected from Cl, Br, I, F, $CF_3$ or $C_{1-3}$ alkyl;

$R^2$ is
1) phenyl,
2) —$NR^3R^4$, wherein $R^3$ and $R^4$ are independently $C_{1-3}$ alkyl or $C_{5-7}$ cycloalkyl.
3) $C_{1-5}$ alkyl or
4) $C_{5-6}$ cycloalkyl.

* * * * *